United States Patent [19]

Horner et al.

[11] 4,455,442

[45] Jun. 19, 1984

[54] PREPARATION OF UNSATURATED ALCOHOLS

[75] Inventors: Michael Horner, Neustadt; Matthias Irgang, Mannheim; Axel Nissen, Leimen, all of Fed. Rep. of Germany

[73] Assignee: BASF Aktiengesellschaft, Fed. Rep. of Germany

[21] Appl. No.: 166,857

[22] Filed: Jul. 8, 1980

[30] Foreign Application Priority Data

Aug. 24, 1979 [DE] Fed. Rep. of Germany ....... 2934251

[51] Int. Cl.$^3$ ...................... C07C 29/14; C07C 33/02; C07C 33/03; C07C 33/20
[52] U.S. Cl. .................... 568/875; 568/813; 568/881
[58] Field of Search .................. 568/875, 881, 813

[56] References Cited

U.S. PATENT DOCUMENTS

| | | | |
|---|---|---|---|
| 3,284,517 | 11/1966 | Rylander et al. | 568/881 |
| 3,655,777 | 4/1972 | Rylander et al. | 568/881 |
| 3,953,524 | 4/1976 | Steiner | 568/875 |
| 4,041,083 | 8/1977 | Gradeff et al. | 568/875 |
| 4,073,813 | 2/1978 | Cordier | 568/875 |
| 4,100,180 | 7/1978 | Ichikawa et al. | 568/875 |

FOREIGN PATENT DOCUMENTS

| | | |
|---|---|---|
| 837057 | 1/1976 | Belgium . |
| 2412517 | 10/1974 | Fed. Rep. of Germany . |
| 2650046 | 6/1977 | Fed. Rep. of Germany ...... 568/881 |
| 38-25654 | 12/1963 | Japan .................................. 568/875 |
| 1123837 | 8/1968 | United Kingdom ................ 568/881 |

OTHER PUBLICATIONS

Bakhanova et al., "Izv. Akad. SSR, Ser. Khima", (1972), pp. 1934–1938.
Rylander et al., "Tetrahedron Letters", No. 20, (1969), pp. 1579, 1580.
Tuley et al., "J. Amer. Chem. Soc.", 47, (1925), pp. 3061–3068.

*Primary Examiner*—J. E. Evans
*Attorney, Agent, or Firm*—Keil & Weinkauf

[57] ABSTRACT

Olefinically unsaturated alcohols (I) are prepared by selective hydrogenation of the corresponding carbonyl compounds (II) in the liquid phase with hydrogen, using an Ru, Rh, Os, Ir or Pt catalyst and carrying out the hydrogenation in the presence of from 5 to 40% by weight, based on (II), of a tertiary amine.

The process is of particular importance for the selective hydrogenation of $\alpha,\beta$-unsaturated carbonyl compounds (IIa) and amongst these specifically for the hydrogenation of citral to geraniol and nerol.

The preferred amine is trimethylamine.

4 Claims, No Drawings

PREPARATION OF UNSATURATED ALCOHOLS

The present invention relates to an improved process for the preparation of olefinically unsaturated alcohols (I) by selective hydrogenation of the corresponding carbonyl compounds (II) in the liquid phase with hydrogen in the presence of a ruthenium, rhodium, osmium, iridium or platinum catalyst.

Specifically, the invention relates to the preparation of unsaturated alcohols of the general formula Ia

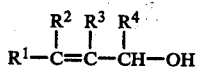  Ia where $R^1$ is hydrogen or an organic radical and $R^2$, $R^3$ and $R^4$ are hydrogen or $C_1$-$C_4$-alkyl, by selective hydrogenation of α,β-unsaturated carbonyl compounds (IIa)

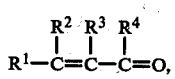  IIa the hydrogenation of citral (IIb)

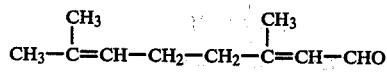  IIb to give geraniol and nerol (respectively E- and Z-3,7-dimethylocta-2,6-dien-1-ol; E-Ib and Z-Ib)

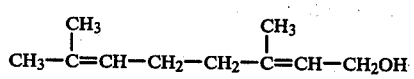  Ib being of particular importance.

It is known from Bakhanova et al., Izv. Akad. Nauk SSR, Ser. Khim 9 (1972), pages 1934 et seq., that geraniol (E-Ib) may be prepared by hydrogenating citral (IIb) with hydrogen in the presence of an iridium catalyst. However, this process has the disadvantage that a disproportionately large amount of the expensive noble metal is required, namely about 4% by weight of iridium, based on the aldehyde to be hydrogenated. The use of osmium as a catalyst for the hydrogenation of unsaturated aldehydes, as recommended in Tetrahedron Letters 20 (1969), 1579 et seq., suffers from the same disadvantage. In this case, 1 g of an Os/active charcoal catalyst, containing 5% by weight of Os, is required for the hydrogenation of 10 g of cinnamaldehyde, i.e. the amount of pure osmium required is 0.5% by weight, and this value is much too high for satisfactory industrial economics.

In addition, J. Am. Chem. Soc. 47 (1925), 3061 et seq. discloses the hydrogenation of cinnamaldehyde by means of platinum catalysts, but the selectivity in respect of cinnamyl alcohol is unsatisfactory. Only if platinum is used together with other catalyst components, such as iron and zinc (Belgian Pat. No. 837,057), iron and silver (U.S. Pat. No. 3,284,517) or cobalt (German Laid-Open Application DOS No. 2,412,517), for the hydrogenation of unsaturated aldehydes, can the formyl group be selectively hydrogenated. Such catalyst systems are however very sensitive and rapidly lose either their activity or their selectivity. This observation conforms to the assertion in German Laid-Open Application DOS No. 2,650,046, page 11, that the above shortcoming is eliminated by using a platinum catalyst which has been pretreated with hydrogen at an elevated temperature. However, this pretreatment is troublesome to carry out industrially, since it either requires a long time or a high pressure of hydrogen. Furthermore, even such a pretreatment does not satisfactorily solve the hydrogenation problem, because if such a catalyst is used repeatedly, different reaction times and greatly differing results are obtained from cycle to cycle, so that a steady production operation is virtually impossible in practice.

It is an object of the present invention to improve, with minimum technical effort and expense, the selectivity of the hydrogenation of unsaturated aldehydes (II) to the corresponding unsaturated alcohols (I) and to ensure, again with minimum effort and expense, that both the activity and the selectivity of the catalyst are maintained for long periods of operation.

We have found that this object is achieved by an improved process for the preparation of the unsaturated alcohols (I) by selective hydrogenation of the carbonyl compounds (II) with hydrogen in the presence of a noble metal catalyst, wherein the catalyst used is a ruthenium, rhodium, osmium, iridium or platinum catalyst and the hydrogenation is carried out in the presence of from 5 to 40% by weight, based on (II), of a tertiary amine.

By employing the above measure, the process proceeds more successfully and there is a substantial saving in noble metal catalyst, compared to conventional processes. Furthermore, the selectivity in respect of product (I) is improved and is maintained at its original high level for long periods of operation; this is particularly important in the case of fragrances and aromatics, eg. citronellal, since, if an acceptably inexpensive method of purification of the product is used, the yield of the desired product diminishes substantially.

According to our observations to date, it is in principle possible to use any tertiary amine, so that the chemical nature of the amine is immaterial, provided it is free from functional groups which may undergo different reactions with the reactants. Examples of suitable tertiary amines include aliphatic tertiary amines of a total of 3 to 30 carbon atoms, especially trimethylamine, but also triethylamine, triethanolamine and trihexylamine, cyclic tertiary amines, eg. N-methylpiperidine, N-methylmorpholine and N,N'-dimethylpiperazine, aliphatic-cycloaliphatic tertiary amines, eg. N,N-dimethylcyclohexylamine, aliphatic-araliphatic tertiary amines, eg. N,N-dimethylbenzylamine, aliphatic-aromatic tertiary amines, eg. N,N-dimethylaniline and heterocyclic-aromatic tertiary amines, eg. pyridine and quinoline.

For economic reasons, the amines to be used are very cheap and have a boiling point which is either substantially lower or substantially higher than that of the product, since in these cases either the amine or the product can easily be distilled from the reaction mixture.

The amount of amine is preferably from 25 to 40% by weight of the starting material (II).

Suitable hydrogenation catalysts are all noble metal catalysts of group VIII of the periodic table, with the exception of palladium, which results in preferred hydrogenation of the olefinic group in the α,β-position. The other noble metals, as defined, which can be used may be in the form of an unsupported or, preferably, of a supported catalyst, and it is a particular advantage that according to our observations to date all commercial catalysts containing such metals are of similar suitability. Hence, if the type of catalyst is changed, the operating conditions need only slight modification, if any. Particularly good results in respect of activity and selectivity are achieved with a ruthenium/active charcoal catalyst which has an inner surface area (measured by the BET method) of 600–900 m²/g.

Expressed as amount of metal based on amount of starting compound (II), preferably from 0.0001 to 0.1, especially from 0.001 to 0.1, % by weight is used.

Since most commercial catalysts are supported catalysts containing 5% by weight of metal on active charcoal as the carrier, such catalysts are preferred, for economic reasons.

The reaction is preferably carried out in the presence of a solvent. The amount of solvent is in general from 10 to 300, preferably from 25 to 150, % by weight of (II). Suitable solvents are all inert liquids in which (I), (II) and the tertiary amine are soluble. Examples include the tertiary amines themselves, as well as alcohols, eg, methanol and ethanol, ethers, acetone and hydrocarbons which are liquid under the reaction conditions, eg. hexane and cyclohexane. Methanol is preferred, especially if trimethylamine is used as the tertiary amine, since in this case working up of the reaction mixtures is particularly simple.

In other respects the hydrogenation is carried out in a conventional manner, ie. at from 20° to 150° C. and under a pressure of from 20 to 200 bar if less than 0.1% by weight, based on (II), of catalyst metal is used, and under a pressure of from 1 to 150 bar if the amount of catalyst is greater than 0.1% by weight.

The novel process is of particular importance for the hydrogenation of citral (IIb) to geraniol and nerol (respectively (E-Ib) and (Z-Ib)), since this reaction is known normally to present technical problems due to multiple hydrogenation and isomerization taking place as competing reactions.

The process is however equally applicable to other compounds (II), and in most cases again offers the above advantages over conventional processes, this being true in almost every case of compounds (IIa), whose olefinic double bonds, being conjugated with the carbonyl group, are hydrogenated particularly easily.

In principle, the radicals $R^1$ in compounds (IIa) may be of any type. If such radicals contain additional olefinic double bonds, these bonds are not attacked. Examples of $R^1$ are alkyl and alkenyl of 1 to 20 carbon atoms and aromatic radicals, eg. phenyl. These radicals may in turn be substituted, for example by alkyl, alkoxy, carbalkoxy, acyl, hydroxyl, carboxyl, nitrile, amino and halogen. Since the principle of the process is unaffected by the nature of the substituents $R^1$ to $R^3$, a detailed recital of the possible starting compounds (IIa) is superfluous. This is also true for the general category of starting compounds (II), where the essential criterion is the presence of one or more olefinic double bonds which on hydrogenation of the carbonyl group are not attacked significantly, if at all. In other respects, the chemical nature is immaterial, but in practice the compounds to be hydrogenated are in most cases unbranched or branched mono-unsaturated or polyunsaturated alkenals and alkenones of 4 to 40 carbon atoms.

EXAMPLE 1

Partial hydrogenation of citral 20 g portions of pure citral were hydrogenated under a variety of conditions, using, in every case, a commercial supported catalyst containing 5% by weight of metal on active charcoal as the carrier.

The reaction conditions and the results of the individual experiments are shown in Table 1. Comparative experiments are marked "C".

The yields of the products were determined gas-chromatographically and the residue gravimetrically.

TABLE 1

| Experiment No. | Catalyst | % by weight[3] | Methanol g | Amine g | | Pressure bar | Temp. °C. | Duration h | Conversion[1] % | Yield[2], % Geraniol/nerol | Citronellol | Residue |
|---|---|---|---|---|---|---|---|---|---|---|---|---|
| 1 | Ir | 0.02 | 16 | NMe₃[4] | 8 | 100 | 50 | 8 | 100 | 93 | 6 | 1 |
| 1C | Ir | 0.02 | 16 | — | — | 100 | 50 | 5 | 90 | 76 | 23 | 1 |
| 2 | Os | 0.02 | 16 | NMe₃ | 8 | 100 | 50 | 7 | 99 | 92 | 7 | 1 |
| 2C | Os | 0.02 | 16 | — | — | 100 | 50 | 5 | 100 | 71 | 28 | 1 |
| 3 | Ru | 0.02 | 16 | NMe₃ | 8 | 100 | 50 | 6 | 100 | 93 | 6 | 1 |
| 3C | Ru | 0.02 | 16 | — | — | 100 | 50 | 5 | 100 | 60 | 39 | 1 |
| 4 | Pt | 0.02 | 16 | NMe₃ | 8 | 100 | 50 | 6 | 100 | 91 | 8 | 1 |
| 4C | Pt | 0.02 | 16 | — | — | 100 | 50 | 7 | 93 | 71 | 28 | 1 |
| 5 | Rh | 0.02 | 16 | NMe₃ | 8 | 100 | 50 | 7 | 99 | 86 | 12 | 1 |
| 5C | Rh | 0.02 | 16 | — | | 100 | 50 | 5 | 100 | 63 | 35 | 2 |
| 6 | Os | 0.1 | 16 | NMe₃ | 8 | 50 | 50 | 8 | 99 | 89 | 10 | 1 |
| 7 | Os | 1.1 | 16 | NMe₃ | 8 | 10 | 50 | 15 | 100 | 93 | 6 | 1 |
| 8 | Os | 0.02 | 16 | NEt₃[5] | 8 | 100 | 100 | 6 | 100 | 92 | 6 | 2 |
| 9 | Os | 0.02 | 0 | NEt₃[5] | 8 | 100 | 100 | 7 | 99 | 91 | 8 | 1 |
| 10 | Os | 0.02 | 16 | NProp₃[6] | 8 | 100 | 100 | 5 | 98 | 90 | 9 | 1 |
| 11 | Os | 0.02 | 16 | NBut₃[7] | 8 | 100 | 100 | 5 | 100 | 90 | 9 | 1 |
| 12 | Os | 0.02 | 16 | Pyridine | 8 | 100 | 100 | 6 | 98 | 89 | 9 | 2 |
| 13 | Os | 0.02 | 16 | Dimethylaniline | 8 | 100 | 100 | 6 | 97 | 89 | 9 | 2 |
| 14 | Os | 0.02 | 16 | N—Methylpiperidine | 8 | 100 | 100 | 5 | 99 | 92 | 7 | 1 |
| 15 | Ru | 0.1 | 16 | NMe₃ | 2 | 50 | 100 | 8 | 99 | 88 | 11 | 1 |
| 16 | Ru | 0.1 | 16 | NMe₃ | 8 | 50 | 100 | 8 | 100 | 93 | 6 | 1 |
| 17 | Ru | 0.1 | 16 | NMe₃ | 16 | 50 | 100 | 8 | 100 | 95 | 4 | 1 |
| 18 | Ru[8] | 0.02 | 16 | NMe₃ | 8 | 100 | 50 | 6 | 100 | 94 | 5 | 1 |
| 19 | Ru[9] | 0.02 | 16 | NMe₃ | 8 | 100 | 50 | 7 | 100 | 93 | 6 | 1 |

TABLE 1-continued

| Experiment No. | Catalyst % by weight[3] | Methanol g | Amine g | Pressure bar | Temp. °C | Duration h | Conversion[1] % | Yield[2], % Geraniol/nerol | Citronellol | Residue |
|---|---|---|---|---|---|---|---|---|---|---|
| 20 | Ru[10] 0.02 | 16 | NMe₃ | 8 | 100 | 50 | 7 | 100 | 94 | 5 | 1 |

[1] based on aldehyde employed
[2] based on conversion
[3] based on aldehyde employed
[4] Me = methyl
[5] Et = ethyl
[6] Prop = n-Propyl
[7] But = n-Butyl
[8] Catalyst recycled 4 times
[9] Catalyst recycled 9 times
[10] Catalyst recycled 15 times

EXAMPLE 2

Partial hydrogenation of citronellal 20 g portions of pure citronellal (3,7-dimethyloct-6-en-1-al) were hydrogenated by a method similar to Example 1.

The reaction conditions and the results are shown in Table 2.

TABLE 2

| Experiment No. | Catalyst % by weight[3] | Methanol g | Amine g | Pressure bar | Temp. °C | Duration h | Conversion[1] % | Yield[2], % Citronellol | 3,7-Dimethyl-octanal | Residue |
|---|---|---|---|---|---|---|---|---|---|---|
| 1 | Ir 0.02 | 16 | NMe₃[4] | 8 | 100 | 100 | 4 | 100 | 97 | 1[11] | 1 |
| 2 | Os 0.02 | 16 | NMe₃[4] | 8 | 100 | 100 | 5 | 99 | 97 | 2 | 1 |
| 3 | Pt 0.02 | 16 | NMe₃[4] | 8 | 100 | 100 | 5 | 98 | 96 | 3 | 1 |
| 4 | Ru 0.02 | 16 | NMe₃[4] | 8 | 100 | 100 | 6 | 100 | 95 | 3 | 1 |
| 5 | Ru 0.02 | 16 | NMe₃[4] | 8 | 100 | 100 | 10 | 100 | 98 | 1 | 1 |
| 6 | Rh 0.02 | 16 | NMe₃[4] | 8 | 100 | 100 | 7 | 100 | 92 | 6 | 2 |
| 7 | Ru 0.02 | 0 | NEt₃[5] | 8 | 100 | 100 | 6 | 98 | 97 | 2 | 1 |
| 8 | Ru 0.02 | 16 | NEt₃[5] | 8 | 100 | 100 | 5 | 100 | 97 | 2 | 1 |
| 9 | Ru 0.02 | 16 | NBut₃[7] | 8 | 100 | 100 | 6 | 95 | 98 | 1 | 1 |
| 10 | Ru 0.02 | 16 | Dimethyl-aniline | 8 | 100 | 100 | 7 | 99 | 96 | 3 | 1 |
| 11 | Ru 0.6 | 16 | NMe₃ | 8 | 5 | 50 | 11 | 100 | 97 | 2 | 1 |
| 12 | Ru 0.01 | 16 | NMe₃ | 8 | 100 | 100 | 7 | 100 | 97 | 2 | 1 |
| 13 | Ru[8] 0.02 | 16 | NMe₃ | 8 | 50 | 100 | 9 | 100 | 98 | 1 | 1 |
| 14 | Ru[9] 0.02 | 16 | NMe₃ | 8 | 50 | 100 | 10 | 99 | 97 | 1 | 1 |
| 15 | Ru[10] 0.02 | 16 | NMe₃ | 8 | 50 | 100 | 11 | 100 | 97 | 2 | 1 |

Footnotes (1) to (10) - see Table 1
[11] in each of Experiments 1 to 12, from 0.5 to 1.5% of 2-isopropenyl-5-methyl-cyclohexen-1-ol (isophlegol) was also found.

EXAMPLES 3–7

Partial hydrogenation of various α,β-unsaturated aldehydes.

Using a method similar to Example 1, 20 g portions of various α,β-unsaturated aldehydes were hydrogenated to the corresponding unsaturated alcohols.

The experimental conditions and the results are shown in Table 3.

We claim:

1. In a process for the preparation of olefinically unsaturated alcohols (I) by selective hydrogenation of the corresponding unsaturated carbonyl compound (II) in the liquid phase with hydrogen in the presence of a noble metal catalyst, the improvement which comprises using as the catalyst ruthenium, rhodium, osmium, iridium or platinum and carrying out the hydrogenation in the presence of from 5 to 40% by weight, based on (II), of a tertiary amine.

2. The process of claim 1, wherein an unsaturated alcohol of the formula Ia

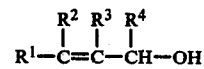

TABLE 3

| Example No. | Aldehyde | Catalyst % by weight[3] | Methanol g | Amine g | Pressure bar | Temp. °C | Duration h | Conversion[1] % | Alcohol | Yield[2] % | Residue |
|---|---|---|---|---|---|---|---|---|---|---|---|
| 3 | Crotonaldehyde | Os 0.02 | 16 | NMe₃[4] | 7 | 50 | 50 | 11 | 98 | But-2-en-1-ol | 85 | 5 |
| 4 | 3-Methyl-crotonaldehyde | Ru 0.02 | 16 | NMe₃[4] | 8 | 50 | 100 | 12 | 98 | 3-Methylbut-2-en-1-ol | 95 | 1 |
| 5 | Cinnamaldehyde | Pt 0.02 | 16 | NMe₃[4] | 8 | 100 | 100 | 6 | 100 | Cinnamyl alcohol | 96 | 1 |
| 6 | α-Methyl-p-tert.-butyl-cinnamaldehyde | Ru 0.02 | 16 | NMe₃[4] | 8 | 100 | 100 | 8 | 100 | α-Methyl-p-tert.-butyl-cinnamyl alcohol | 93 | 1 |
| 7 | 3,7-Dimethyl-nona-2,6-dien-1-al | Ru 0.02 | 16 | NMe₃[4] | 8 | 50 | 100 | 9 | 99 | 3,7-Dimethyl-nona-2,6-dien-1-ol | 94 | 1 |

Footnotes (1) to (4) - see Table 1 where $R^1$ is hydrogen or an organic radical and $R^2$, $R^3$ and $R^4$ are hydrogen or $C_1$–$C_4$-alkyl is prepared from the corresponding α,β-unsaturated carbonyl compounds (IIa)
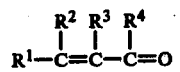
3. The process of claim 2, wherein citral (IIb) is hydrogenated to geraniol (E-Ib) and nerol (Z-Ib).
4. The process of claim 1 or 2 or 3, wherein trimethylamine is used as the tertiary amine.
* * * * *